United States Patent
Yamamoto et al.

(10) Patent No.: US 11,533,887 B2
(45) Date of Patent: Dec. 27, 2022

(54) ABSORBENT SHEET FOR PETS

(71) Applicant: UNICHARM CORPORATION, Ehime (JP)

(72) Inventors: Hiroki Yamamoto, Kagawa (JP); Ayano Okawa, Kagawa (JP); Yasuhiro Sasano, Kagawa (JP); Shinya Kaneko, Kagawa (JP)

(73) Assignee: Unicharm Corporation, Ehime (JP)

( * ) Notice: Subject to any disclaimer, the term of this patent is extended or adjusted under 35 U.S.C. 154(b) by 321 days.

(21) Appl. No.: 16/878,956

(22) Filed: May 20, 2020

(65) Prior Publication Data
US 2020/0367465 A1    Nov. 26, 2020

(30) Foreign Application Priority Data

May 20, 2019  (JP) .............................. JP2019-094872

(51) Int. Cl.
*A61F 13/513*   (2006.01)
*A01K 1/01*    (2006.01)
(Continued)

(52) U.S. Cl.
CPC .......... *A01K 1/0107* (2013.01); *A61F 13/513* (2013.01); *A61F 13/515* (2013.01);
(Continued)

(58) Field of Classification Search
CPC ................ A61F 13/511; A61F 13/5113; A61F 13/51121; A61F 13/513; A61F 13/515; A61F 13/5323; A61F 2013/15008; A61F 2013/15186; A61F 2013/15439; A61F 2013/15447; A61F 2013/15455;
(Continued)

(56) References Cited

U.S. PATENT DOCUMENTS

| 5,482,007 A | 1/1996 | Kumlin |
| 2015/0320009 A1 | 11/2015 | Sasano et al. |

FOREIGN PATENT DOCUMENTS

| CN | 104486941 A | 4/2015 |
| CN | 107205360 A | 9/2017 |

(Continued)

OTHER PUBLICATIONS

Extended European Search Report issued in corresponding European Application No. 20174378.8 dated Oct. 19, 2020 (8 pages).

(Continued)

*Primary Examiner* — Catharine L Anderson
(74) *Attorney, Agent, or Firm* — Osha Bergman Watanabe & Burton LLP (57) ABSTRACT

An absorbent sheet for a pet toilet is provided. The pet toilet includes: a sheet accommodating portion that accommodates the absorbent sheet in a space surrounded by a bottom portion and side walls standing from the bottom portion; and an excretion receiving portion that receives excretions above the sheet accommodating portion and guides the excretions to the sheet accommodating portion. The absorbent sheet includes: a topsheet on a top side of the absorbent sheet and that includes fibers; a backsheet on a back side of the absorbent sheet; an absorber between the topsheet and the backsheet; a central region in which the absorber is disposed in plan view; and side regions that extend outside the central region and in which at least the topsheet is disposed.

18 Claims, 7 Drawing Sheets

(51) Int. Cl.
  *A61F 13/511* (2006.01)
  *A61F 13/515* (2006.01)
  *A61F 13/51* (2006.01)
  *A61F 13/53* (2006.01)
  *A61F 13/84* (2006.01)

(52) U.S. Cl.
  CPC .............. *A61F 13/51121* (2013.01); *A61F 2013/51002* (2013.01); *A61F 2013/530007* (2013.01); *A61F 2013/530883* (2013.01); *A61F 2013/8414* (2013.01)

(58) Field of Classification Search
  CPC .. A61F 2013/51002; A61F 2013/51007; A61F 2013/51054; A61F 2013/51152; A61F 2013/51047; A61F 2013/8414
  See application file for complete search history.

(56) References Cited

FOREIGN PATENT DOCUMENTS

| | | |
|---|---|---|
| JP | 2006-000102 A | 1/2006 |
| JP | 2007-000124 A | 1/2007 |
| JP | 2008-237185 A | 10/2008 |
| JP | 2009-011180 A | 1/2009 |
| JP | 2009-118791 A | 6/2009 |
| JP | 2012-144835 A | 8/2012 |
| JP | 2013-128453 A | 7/2013 |
| JP | 2013-247923 A | 12/2013 |
| WO | 2014/007072 A1 | 1/2014 |
| WO | 2014/091872 A1 | 6/2014 |
| WO | 2019/092891 A1 | 5/2019 |

OTHER PUBLICATIONS

Decision to Grant a Patent issued in corresponding Japanese Application No. 2019-094872 dated Apr. 26, 2022 (5 pages).

Office Action issued in corresponding European Application No. 20174378.8 dated Oct. 19, 2021 (6 pages).

Notice of Reasons for Refusal issued in corresponding Japanese Application No. 2019-094872 dated Jan. 11, 2022 (12 pages).

Office Action issued in corresponding European Application No. 20174378.8 dated Jun. 14, 2022 (7 pages).

ABSORBENT SHEET FOR PETS

CROSS-REFERENCE TO RELATED APPLICATIONS

The entire contents of Japanese Patent Application No. 2019-094872 (filed on May 20, 2019) are incorporated herein by reference.

TECHNICAL FIELD

The present invention relates to an absorbent sheet for pets used for a toilet for pets such as dogs.

BACKGROUND

An absorbent sheet for pets used in a pet toilet has been known (see Patent Literature 1 below). The pet toilet of Patent Literature 1 includes a box-shaped toilet sand storage container for storing toilet sand, a sheet accommodating portion which is located below the toilet sand storage container and is detachably incorporated, and a side cover installed so as to cover the side surfaces above the toilet sand storage container. An absorbent sheet is arranged in the sheet accommodating portion. Animal excretions penetrate the toilet sand of the toilet sand storage container and are guided to the absorbent sheet.

The sheet accommodating portion has a substantially square bottom portion, and four side wall portions arranged to stand from the four sides of the bottom portion at a predetermined angle with respect to the bottom portion. The absorbent sheet is arranged in the sheet accommodating portion and absorbs a bodily fluid guided into the sheet accommodating portion.

PATENT LITERATURE

Patent Literature 1: JP 2007-124 A

When a pet toilet as disclosed in Patent Literature 1 is used, a user places the absorbent sheet in the sheet accommodating portion. At this time, when the size of the absorbent sheet is larger than the size of the bottom portion, the absorbent sheet is arranged along the bottom portion and the side wall portions. Further, even when the size of the absorbent sheet is equal to or smaller than the size of the bottom portion, the absorbent sheet is arranged along the bottom portion and the side wall portions depending on the position where the absorbent sheet is arranged. At this time, if the absorbent sheet is not arranged along the bottom portion and the side wall portions, the absorbent sheet rises from the bottom portion, and there is a fear that the space for accommodating excretions is reduced, or the position of the absorbent sheet is unintentionally shifted. In particular, when the absorbent sheet is pulled out together with the sheet accommodating portion, there is a feat that the position of the absorbent sheet is unintentionally shifted.

When the position of the absorbent sheet is shifted, the absorbent sheet may not be able to absorb the bodily fluid, or the bodily fluid may leak out of the absorbent sheet, so that the absorbent sheet may not be able to absorb the bodily fluid sufficiently.

SUMMARY

One or more embodiments of the present invention provide an absorbent sheet for pets that can suppress displacement in a pet toilet.

An absorbent sheet for pets according to one or more embodiments is the absorbent sheet for pets used for a pet toilet. The pet toilet including a sheet accommodating portion configured to accommodate the absorbent sheet in a space surrounded by a bottom portion and side wall portions (side walls) standing from the bottom portion, and an excretion receiving portion configured to receive excretions above the sheet accommodating portion, and guide the excretions to the sheet accommodating portion. The absorbent sheet includes: a topsheet arranged on a top side of the absorbent sheet and having fibers; a backsheet arranged on a back side of the absorbent sheet; an absorber provided between the topsheet and the backsheet; a central region in which the absorber is arranged in plan view; and side regions which extend outside the central region and in which at least the topsheet is arranged. The topsheet has a first surface and a second surface opposite to the first surface. A fiber density of a region on a side of the first surface in the topsheet is lower than a fiber density of a region on a side of the second surface in the topsheet. A surface roughness of the first surface of the topsheet is higher than a surface roughness of the second surface of the topsheet.

DETAILED DESCRIPTION (1) Outline of Embodiments

According to the present specification and the accompanying drawings, at least the following matters will be disclosed.

An absorbent sheet for pets according to one or more embodiments is the absorbent sheet for pets used for a pet toilet. The pet toilet including a sheet accommodating portion configured to accommodate the absorbent sheet in a space surrounded by a bottom portion and side wall portions standing from the bottom portion, and an excretion receiving portion configured to receive excretions above the sheet accommodating portion, and guide the excretions to the sheet accommodating portion. The absorbent sheet includes: a topsheet arranged on a top side of the absorbent sheet and having fibers; a backsheet arranged on a back side of the absorbent sheet; an absorber provided between the topsheet and the backsheet; a central region in which the absorber is arranged in plan view; and side regions which extend outside the central region and in which at least the topsheet is arranged. The topsheet has a first surface and a second surface opposite to the first surface. A fiber density of a region on a side of the first surface in the topsheet is lower than a fiber density of a region on a side of the second surface in the topsheet. A surface roughness of the first surface of the topsheet is higher than a surface roughness of the second surface of the topsheet. According to this aspect, the first surface of the topsheet is flexibly deformed and the second surface maintains the shape along the fold, so that the side regions of the absorbent sheet are easily arranged along the bottom portion and the side wall portions of the sheet accommodating portion. As a result, the displacement of the absorbent sheet in the pet toilet can be suppressed.

According to one or more embodiments, the absorbent sheet has a thickness direction, a first direction perpendicular to the thickness direction, and a second direction perpendicular to the thickness direction and the first direction. Before use, the absorbent sheet is folded with a folding line extending in the second direction as a base point. A length of the absorbent sheet in the first direction is longer than a length of the absorbent sheet in the second direction. The side regions are provided over (i.e., cover) an entire region of the absorbent sheet in the first direction on both sides of the central region in the second direction, and the folding line is formed in the side regions. According to this aspect, since the folding line is formed in the side regions, the rigidity of the side regions increases due to the folding crease of the folding line, and the standing state can be easily maintained. Therefore, the side regions can maintain the state arranged along the bottom portion and the side wall portions, and the displacement of the absorbent sheet in the pet toilet can be suppressed.

According to one or more embodiments, the absorbent sheet has a thickness direction, a first direction perpendicular to the thickness direction, and a second direction perpendicular to the thickness direction and the first direction. A length of the absorbent sheet in the first direction is longer than a length of the absorbent sheet in the second direction. The side regions are provided over an entire region of the absorbent sheet in the first direction on both sides of the central region in the second direction. The topsheet has more fibers oriented along the second direction than fibers oriented along the first direction. According to this aspect, relatively many fibers are oriented along the first direction, and it is easy to continuously form the standing state in the first direction. Therefore, the side regions can maintain the state arranged along the bottom portion and the side wall portions, and the displacement of the absorbent sheet in the pet toilet can be suppressed.

According to one or more embodiments, joining portions that join the topsheet and the backsheet are provided. A plurality of the joining portions extends in the second direction in the side regions and is provided at intervals in the first direction. According to this aspect, since the joining portion extending in the second direction is provided in the side regions, the rigidity along the second direction is increased by the joining portion, and the standing state of the side regions is easily maintained.

According to one or more embodiments, joining portions that join the topsheet and the backsheet are provided. A non-joining region having no joining portion is provided at an outer edge portion (outer edge) of the side region in plan view. In the non-joining region, the topsheet and the backsheet are easily deformed more flexibly in the side regions than in the region where the topsheet and the backsheet are joined. When the absorbent sheet is stored in the sheet accommodating portion or when the sheet accommodating portion is taken in and out, the non-joining region of the absorbent sheet is locally deformed. Thus, the deformation of the entire absorbent sheet is suppressed, and the displacement of the absorbent sheet in the sheet accommodating portion can be suppressed.

According to one or more embodiments, the absorber includes an absorbent core, and a cover sheet arranged between the topsheet and the absorbent core. The cover sheet covers side surfaces of the absorbent core, and is folded back to a top side of the absorbent core. The rigidity difference between the central region and the side regions is further increased by presence or absence of a cover sheet and folding of the cover sheet. The side regions more easily raise with respect to the central region, and the side regions more easily follow the side wall portions.

According to one or more embodiments, the topsheet includes a sheet containing an antimicrobial component. Since the topsheet includes a sheet containing an antibacterial component, an antibacterial function can be exhibited during the passage of a bodily fluid, and the growth of bacteria in the bodily fluid held by the absorbent sheet can be suppressed.

According to one or more embodiments, the absorber includes an absorbent core. The absorbent core includes an upper pulp layer containing pulp, and a lower pulp layer arranged on a side closer to the backsheet than the upper pulp layer and containing pulp. According to this aspect, the upper pulp layer allows the bodily fluid on the topsheet to be quickly drawn in. Further, the drawn bodily fluid can be held by the lower pulp layer. The bodily fluid can be quickly guided from the topsheet side which is closer to a pet to the backsheet side which is farther from the pet.

According to one or more embodiments, the absorber has a superabsorbent polymer disposed between the upper pulp layer and the lower pulp layer. According to this aspect, the bodily fluid is easily drawn in by the superabsorbent polymer, and the bodily fluid can be more quickly guided toward the backsheet side.

(2) Overall Structure of Absorbent Sheet

An absorbent sheet for pets according one or more embodiments will be described below by referring to the accompanying drawings. In the drawings, the same or similar parts are indicated by the same or similar reference signs. The drawings are illustrated schematically, and dimensional ratio and other variables differ from those of actual measurements. The actual measurements or the like, therefore, should be determined by referring to the following description. The drawings may include different relationships or ratios of measurements.

In this specification, "pets" widely include a vertebrate and an invertebrate, and typically include a pet such as a cat, a dog, a rabbit, a hamster, etc. The absorbent sheet for pets according to one or more embodiments is an absorbent sheet for cats.

Figure 1A:
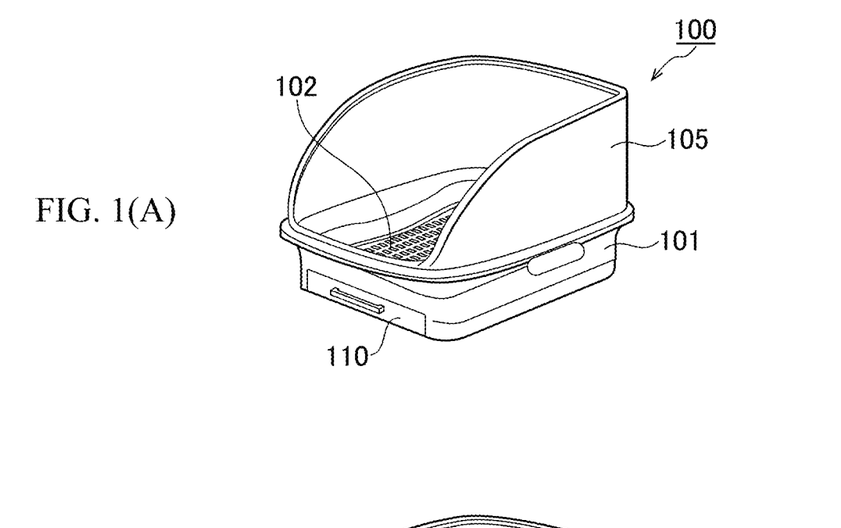
FIGS. 1(A) and 1(B) show one or more embodiments of the pet toilet.
Figure 1B:
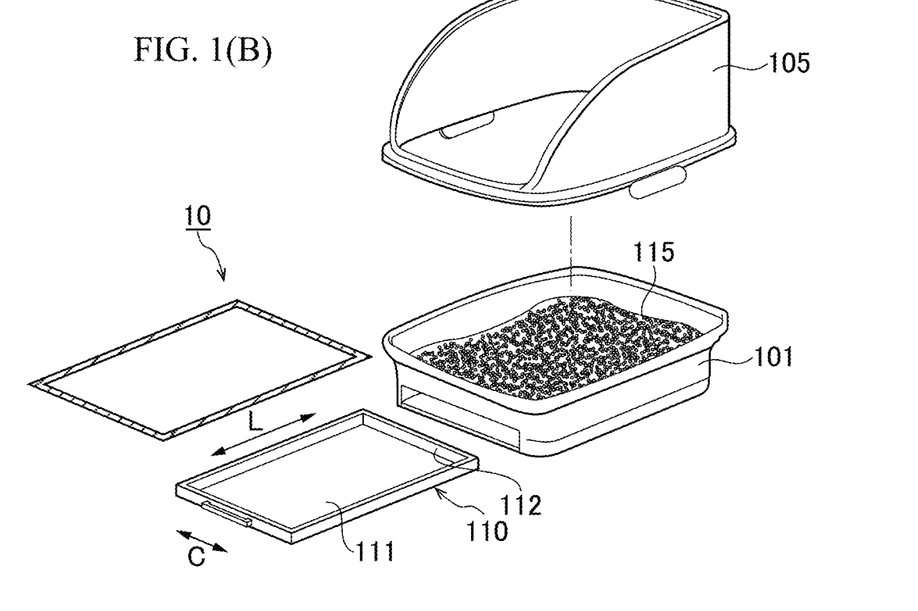

An absorbent sheet 10 according to one or more embodiments of the present invention is an absorbent sheet 10 for pets used for a pet toilet 100. FIGS. 1(A) and (1B) show an embodiment of the pet toilet 100. FIG. 1(A) is a perspective view of the pet toilet 100. As shown in FIG. 1(A), the pet toilet 100 of one or more embodiments includes at least an excretion receiving portion 101 and a sheet accommodating portion 110. The excretion receiving portion 101 receives excretions above the sheet accommodating portion 110 and guides the excretions to the sheet accommodating portion. The excretion receiving portion 101 is a portion that receives excretions of a pet, and may be configured to accommodate toilet sand 115. FIG. 1(B) shows a state where the pet toilet 100 is disassembled and the toilet sand 115 is disposed. The bottom surface of the excretion receiving portion 101 has a plurality of holes 102. The holes 102 have a size that allows a bodily fluid as excretions to permeate without feces as excretions and the toilet sand 115 falling out. The pet toilet 100 may include a cover 105 surrounding the excretion receiving portion 101 above the excretion receiving portion 101. Further, in the excretion receiving portion 101 of one or more embodiments, an accommodating portion for detachably accommodating the sheet accommodating portion 110 and a holding portion for holding toilet sand are integrated. Further, in a modified example, in the excretion receiving portion 101 of one or more embodiments, the accommodating portion for detachably accommodating the sheet accommodating portion 110 and the holding portion for holding toilet sand may be separate bodies and be configured to be separable from each other.

The sheet accommodating portion 110 accommodates the absorbent sheet 10. The sheet accommodating portion 110 accommodates the absorbent sheet 10 in a space surrounded by a bottom portion 111 and side wall portions 112 standing from the bottom portion 111. The sheet accommodating portion 110 may be detachably incorporated in the excretion receiving portion 101. The sheet accommodating portion 110 is substantially rectangular in plan view, and has a longitudinal direction L and a perpendicular direction C perpendicular to the longitudinal direction L.

Figure 2:
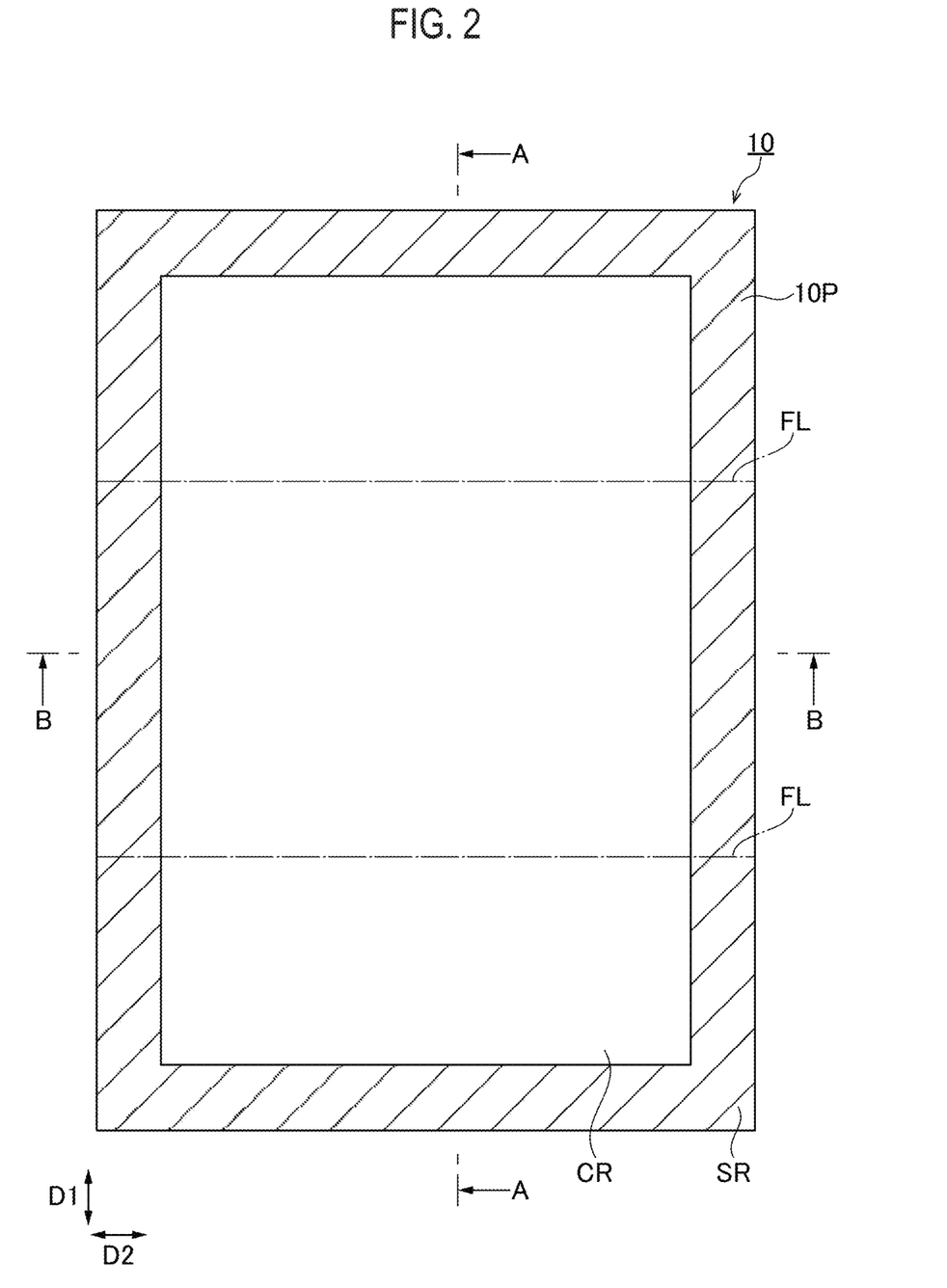
FIG. 2 is a plan view of the absorbent sheet 10 for pets according to one or more embodiments as viewed from the excretion surface side.
Figure 3:
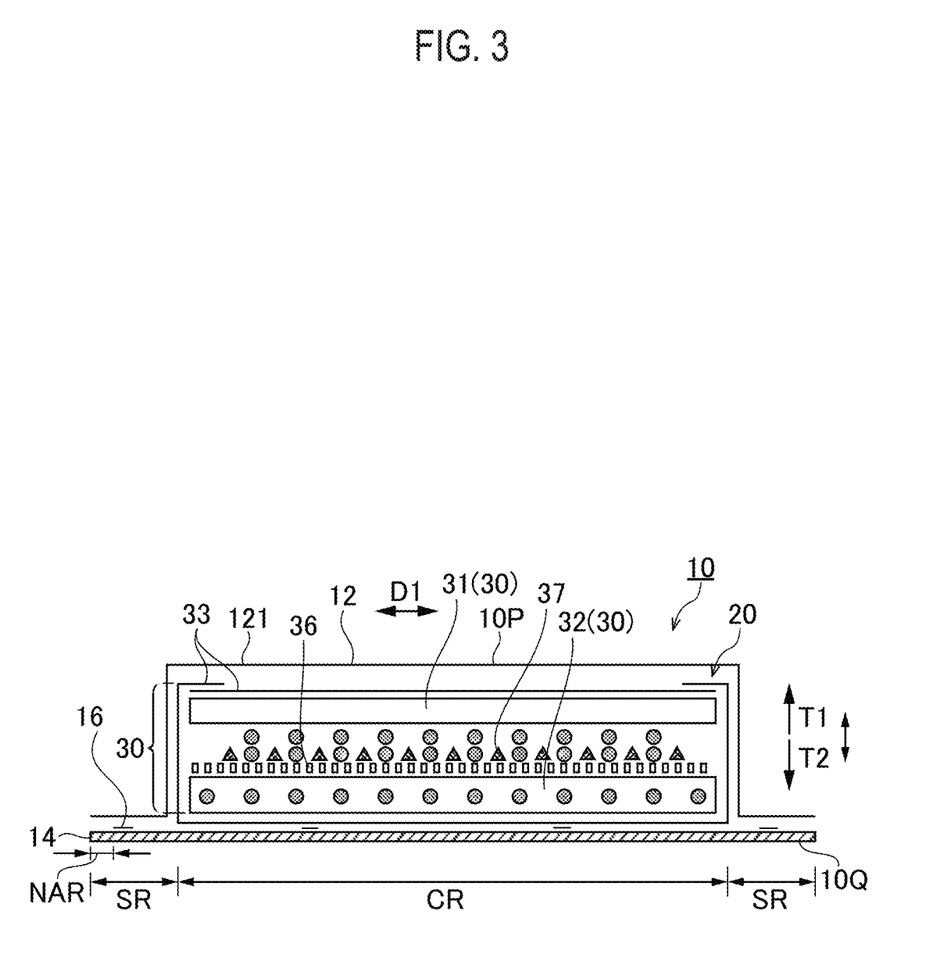
FIG. 3 is a schematic cross-sectional view of the absorbent sheet for pets taken along the line A-A shown in FIG. 2.
Figure 4:
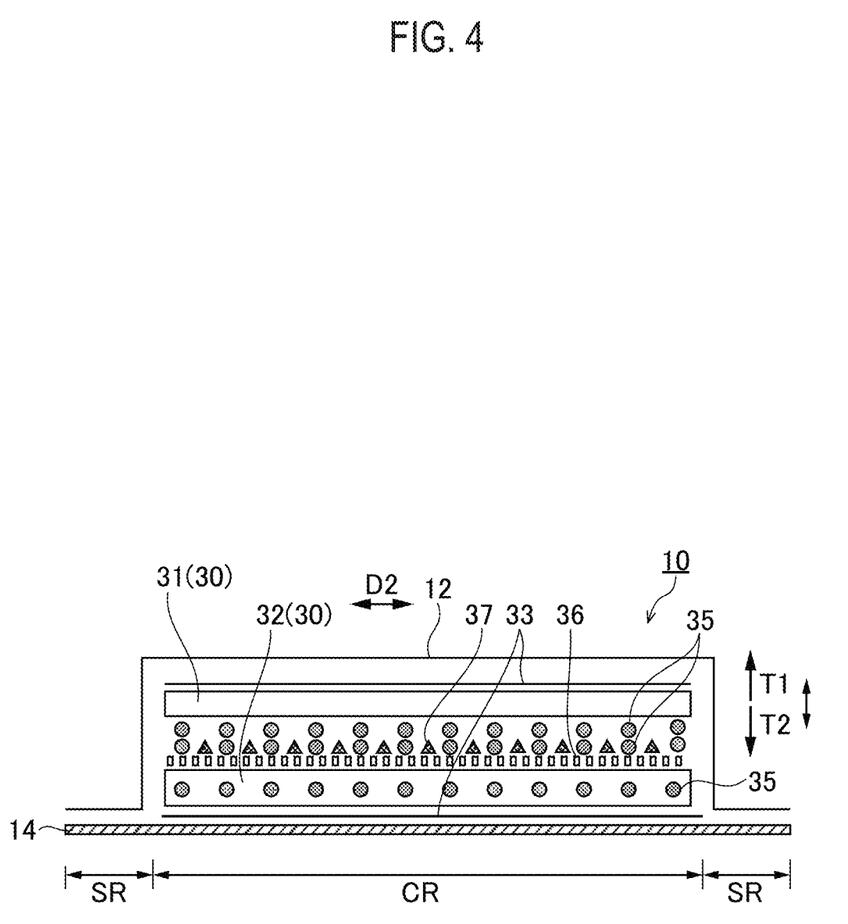
FIG. 4 is a schematic cross-sectional view of the absorbent sheet for pets taken along the line B-B shown in FIG. 2.
Figure 5:
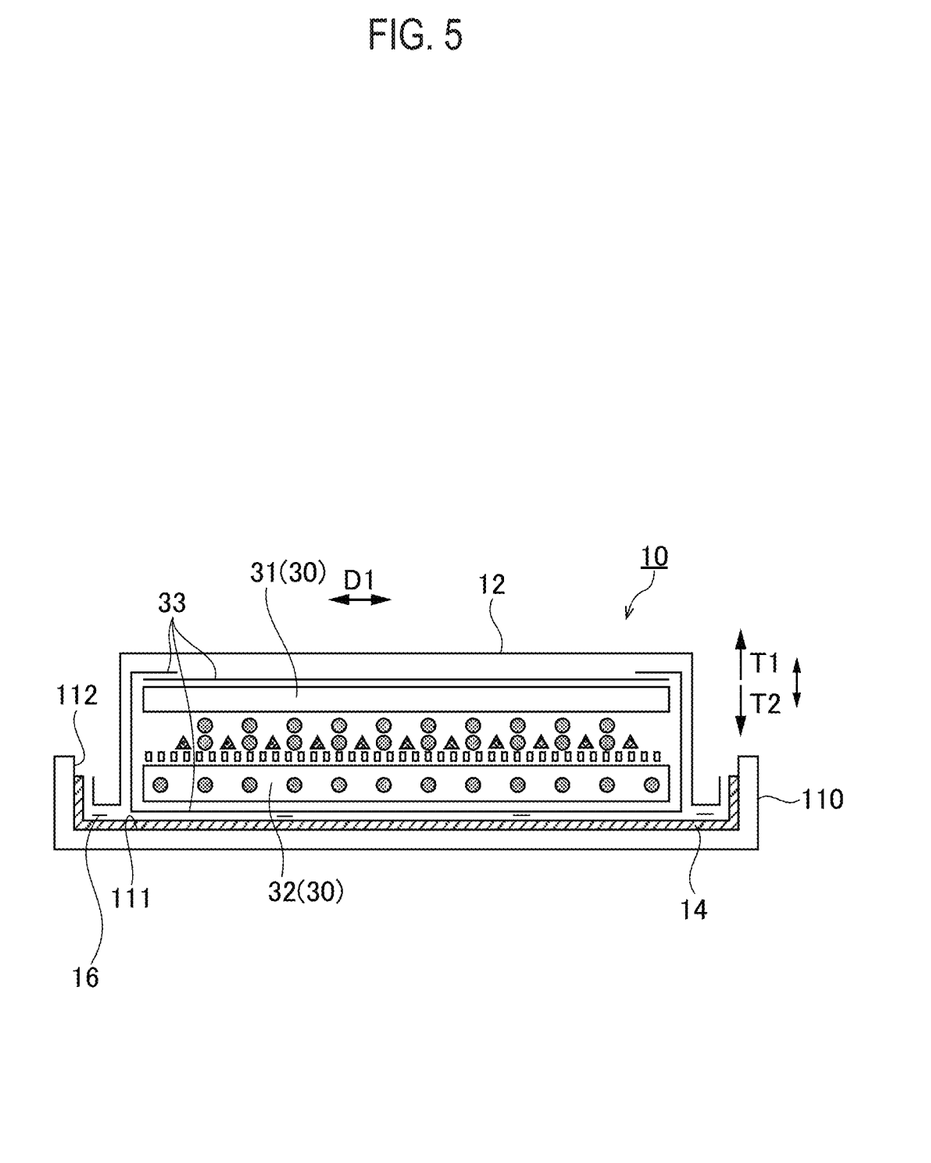
FIG. 5 is a schematic cross-sectional view showing a state where the absorbent sheet is accommodated in the sheet accommodating portion of the pet toilet.

FIG. 2 is a plan view of the absorbent sheet 10 for pets according to one or more embodiments as viewed from the excretion surface side. FIG. 3 is a schematic cross-sectional view of the absorbent sheet 10 for pets taken along the line A-A shown in FIG. 2. FIG. 4 is a schematic cross-sectional view of the absorbent sheet 10 for pets taken along the line B-B shown in FIG. 2. FIG. 5 is a schematic cross-sectional view showing a state where the absorbent sheet 10 is accommodated in the sheet accommodating portion 110 of the pet toilet 100. The absorbent sheet 10 is a generally flat sheet. One surface of the absorbent sheet 10 for pets is an excretion surface that receives excretions of a pet. In one or more embodiments, a surface constituting the excretion surface is referred to as front surface 10P, and a surface constituting a non-excretion surface is referred to as back surface 10Q for description. In FIGS. 3, 4, and 5, a top side T1 and a back side T2 in a thickness direction T are shown.

The absorbent sheet 10 for pets has a first direction D1 and a second direction D2 perpendicular to the thickness direction T. The first direction D1 and the second direction D2 are perpendicular to each other. The first direction D1 and the second direction D2 are directions extending in a plane direction. The first direction D1 of one or more embodiments is a longitudinal direction in plan view, and the second direction D2 is a width direction perpendicular to the longitudinal direction. The length of the absorbent sheet 10 in the first direction D1 may be longer than the length of the absorbent sheet 10 in the second direction D2. In a modified example, the first direction D1 may be a width direction in plan view, and the second direction D2 may be the longitudinal direction. The first direction D1 of the absorbent sheet 10 for pets may be arranged along the longitudinal direction L of the sheet accommodating portion 110. Before use, the absorbent sheet 10 may be folded with folding lines FL extending in the second direction D2 as base points. One folding line FL may be provided, or a plurality of folding lines FL may be provided at intervals in the first direction D1.

The absorbent sheet 10 for pets includes a topsheet 12 arranged on the top side T1, a backsheet 14 arranged on the back side T2, and an absorber 20. The absorber 20 is provided between the topsheet 12 and the backsheet 14.

The topsheet 12 may be a liquid-permeable sheet that is permeable to liquid such as excretions of a pet. The topsheet 12 has fibers and may include a nonwoven fabric or a woven fabric. The backsheet 14 may be an impermeable sheet that is not permeable to liquid such as excretions of a pet. The backsheet 14 is not particularly limited, but may include, for example, a resin film sheet.

The topsheet 12 extends outside the absorber 20. The absorbent sheet 10 has a central region CR in which the absorber 20 is arranged in plan view, and side regions SR which extend outside the central region CR and in which at least the topsheet 12 is arranged. In FIG. 2, the side regions SR are shown by hatching. The side regions SR may be provided in at least one of regions outside the central region CR in the first direction D1 and regions outside the side regions SR in the second direction D2 (i.e., side regions SR may be provided in regions outside the central region CR in the first direction D1 and/or regions outside the side regions SR in the second direction D2). In the side regions SR, at least the topsheet 12 only needs to be arranged, and the backsheet 14 may be arranged. The side regions SR may be provided over the entire regions of the absorbent sheet 10 in the first direction D1 on both sides of the central region CR in the second direction D2, and may be provided over the entire regions of the absorbent sheet 10 in the second direction D2 on both sides of the central region CR in the first direction D1.

The absorber 20 may include an absorbent core 30, and a cover sheet 33 arranged between the topsheet 12 and the absorbent core 30. The cover sheet 33 may cover the bottom surface of the absorbent core 30 and the side surfaces of the absorbent core 30, and may be folded back to the surface side of the absorbent core 30. More specifically, the cover sheet 33 may cover the bottom surface of the absorbent core 30 and the side surfaces of the absorbent core 30 in the first direction D1, and may be folded back to the surface side T1 along the side surface of the absorbent core 30 in the first direction D1. In a modified example, the cover sheet 33 may cover the upper surface of the absorbent core 30 and the side surfaces of the absorbent core 30 in the first direction D1, and may be folded back to the back side T2 along the side surface of the absorbent core 30 in the first direction D1.

The absorbent core 30 is not particularly limited, but may include a hydrophilic fiber layer such as pulp, and a superabsorbent polymer (SAP), or a combination thereof. The cover sheet 33 is not particularly limited, but can be made of, for example, a liquid-permeable tissue.

As shown in FIG. 3, joining portions 16 for joining the topsheet 12 and the backsheet 14 may be provided. The joining portions 16 may join the backsheet 14 and the absorber 20 in a region where the absorber is arranged. The joining portion may include an adhesive such as a hot-melt adhesive, may be formed by heat welding, or may be formed by ultrasonic welding.

Next, the topsheet 12 will be described in detail. The topsheet 12 has a first surface 121 and a second surface 122 opposite to the first surface 121. The fiber density in the region on the first surface 121 side of the topsheet 12 is lower than the fiber density in the region on the second surface side of the topsheet 12. The surface roughness of the first surface 121 of the topsheet 12 is higher than the surface roughness of the second surface 122 of the topsheet 12. The topsheet 12 may include an air-through nonwoven fabric.

Figure 6A:
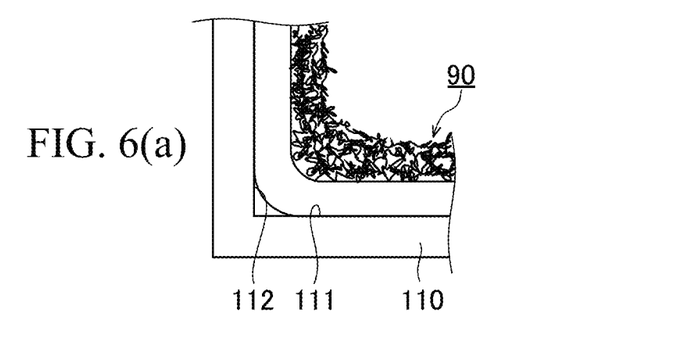
FIGS. 6(a) to 6(c) are diagrams schematically showing a state where the side regions of the absorbent sheet are arranged along the bottom portion and the side wall portions of the sheet accommodating portion.
Figure 6B:
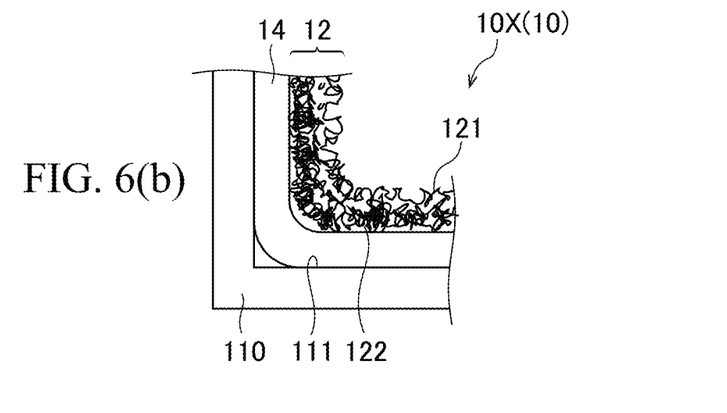
Figure 6C:
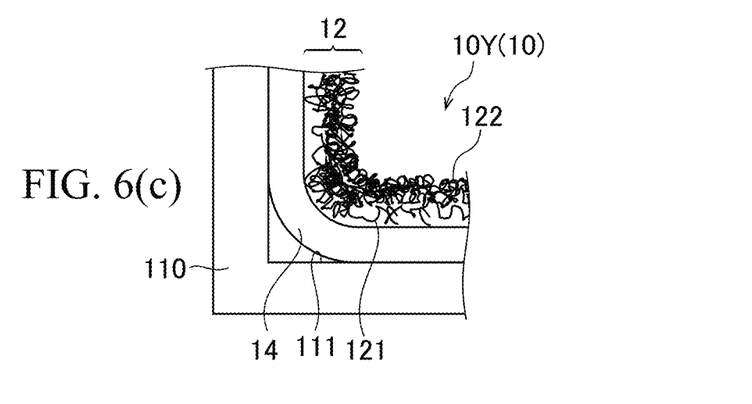
Figure 7A:
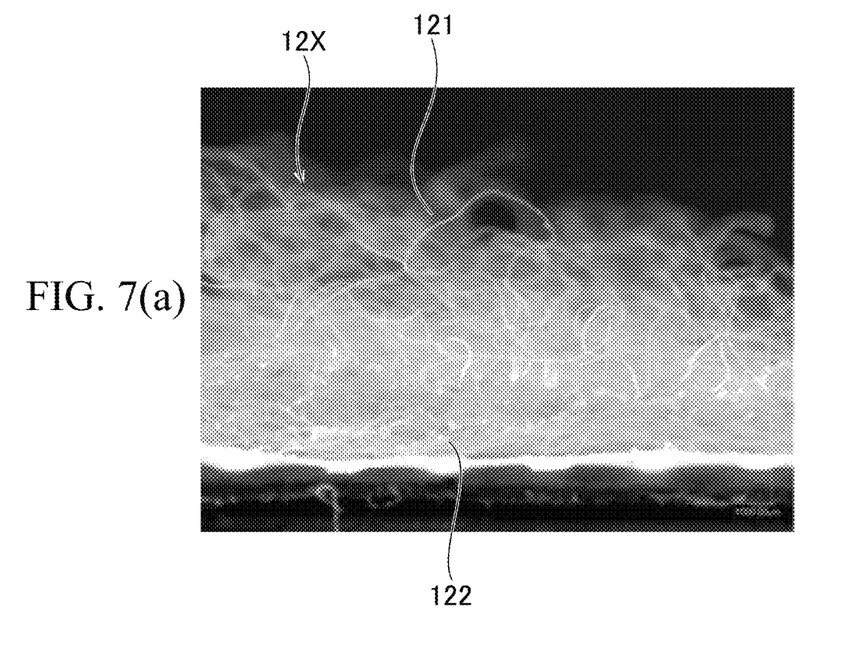
FIGS. 7(a) and 7(b) are enlarged cross-sectional photographs of the topsheet of the absorbent sheet.
Figure 7B:
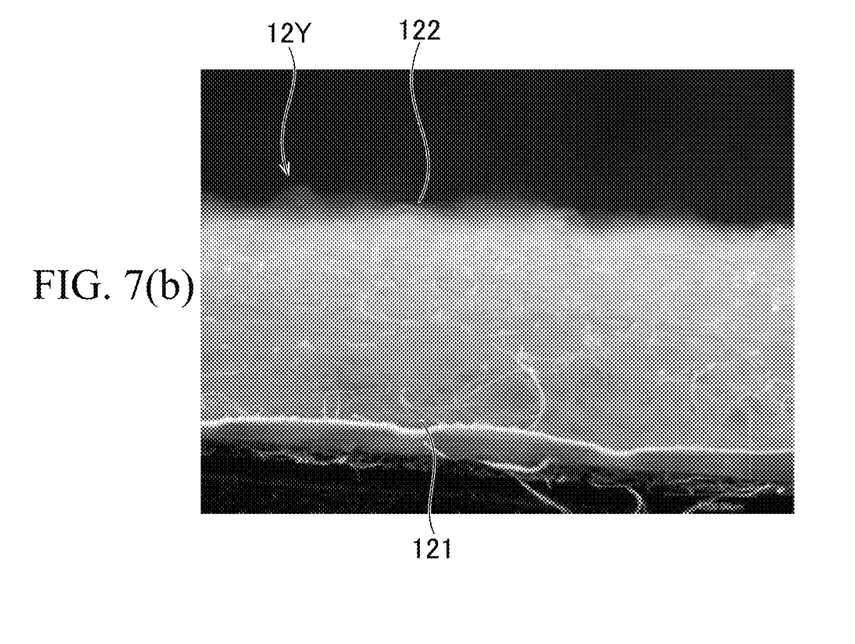

The side regions SR are located outside the central region CR, and may be arranged across the bottom portion 111 and the side wall portions 112 of the sheet accommodating portion 110 in a state where the absorbent sheet 10 is arranged in the sheet accommodating portion 110 of the pet toilet 100. In the side regions SR, a fold is easily formed in a state where the side regions SR are arranged along the bottom portion 111 and the side wall portions 112. FIGS. 6(a) to 6(c) are diagrams schematically showing a state where the side regions SR of the absorbent sheet 10 are arranged along the bottom portion 111 and the side wall portions 112 of the sheet accommodating portion 110. FIG. 6(a) is a diagram schematically showing an absorbent sheet 90 according to a comparative example. FIGS. 6(b) and 6(c) are diagrams schematically showing the absorbent sheet 10 of one or more embodiments. FIG. 6(b) is a diagram schematically showing an absorbent sheet 10X in which the first surface 121 is arranged on the upper side (side opposite to the absorbent core), and the second surface 122 is arranged to be opposed to the bottom portion 111 of the sheet accommodating portion 110. FIG. 6(c) is a diagram schematically showing an absorbent sheet 10Y in which the first surface 121 is arranged on the lower side (absorbent core side), and the first surface 121 is arranged to be opposed to the bottom portion 111 of the pet toilet. FIGS. 7(a) and 7(b) are enlarged cross-sectional photographs of the topsheet of the absorbent sheet. FIG. 7(a) is enlarged cross-sectional photograph of a topsheet 12X in a state where the first surface 121 is arranged on the upper side, and FIG. 7(b) is an enlarged cross-sectional photograph of a topsheet 12Y in a state where the second surface 122 is arranged on the upper side.

In the state where the side regions SR are arranged along the bottom portion 111 and the side wall portions 112, on the first surface 121 side of the absorbent sheet 10, the fiber density is low, and there are few fusion points between fibers. Therefore, the first surface 121 side of the topsheet 12 is easily deformed more flexibly than the second surface 122 side. Further, the first surface 121 has a high surface roughness and large spaces due to the unevenness. Therefore, the first surface 121 side of the topsheet 12 is easily deformed more flexibly than the second surface 122 side by the spaces due to the unevenness.

On the other hand, on the second surface 122 side of the topsheet 12, the fiber density is high, and there are many fusion points between fibers. Therefore, the second surface 122 side of the topsheet 12 is more likely to have a folding crease than the first surface 121 side, and it is easy to maintain the shape along the fold. Further, the second surface 122 has a low surface roughness and small spaces due to the unevenness. Therefore, the second surface 122 side of the topsheet 12 has smaller spaces due to the unevenness than the first surface 121 side, is more likely to have a folding crease, and it is easy to maintain the shape along the fold.

As in the case of the absorbent sheet 90 according to the comparative example shown in FIG. 6(a), when the fiber density is high and the surface roughness is low on both sides of the topsheet, the absorbent sheet is not flexibly deformed and not deformed along fold, and easily returns to the state before being folded. Further, for example, when the fiber density is low and the surface roughness is high on both sides of the topsheet, the shape along the fold cannot be maintained.

In the absorbent sheet 10 of one or more embodiments, the first surface 121 of the topsheet 12 is flexibly deformed and the second surface 122 maintains the shape along the fold, so that the side regions SR are easily arranged along the bottom portion 111 and the side wall portions. As a result, the displacement of the absorbent sheet 10 in the pet toilet 100 can be suppressed.

As shown in FIG. 6(b), the second surface 122 may be a surface arranged to be opposed to the bottom portion 111 of the sheet accommodating portion 110. The first surface 121 is arranged facing upward while being arranged in the pet toilet 100. In a state where the topsheet 12 is folded along the bottom portion 111 and the side wall portions 112 of the sheet accommodating portion 110, the first surface 121 is folded so that the folded parts face each other. At this time, since the fiber density on the first surface 121 side is low and the gaps between the fibers before the first surface 121 is folded is large, the first surface 121 is easily deformed so that the folded parts approach each other due to the decrease in the gaps. Therefore, the topsheet can be deformed along the fold, and is easily arranged along the bottom portion 111 and the side wall portions 112 of the sheet accommodating portion 110. In addition, since the fiber density on the second surface 122 side is high, the portion on the second surface 122 side tends to have a folding crease, and the state along the fold is easily maintained. As a result, the displacement of the absorbent sheet in the pet toilet can be suppressed. In addition, since the surface roughness on the first surface 121 side is high, it is easy to secure a contact area for excretions due to the unevenness of the first surface 121. Therefore, the speed of excretion absorption can be improved.

As shown in FIG. 6(c), the first surface 121 of the topsheet 12 may be a surface arranged to be opposed to the bottom portion 111 of the sheet accommodating portion 110. The first surface 121 is arranged facing downward while being arranged in the pet toilet. In a state where the topsheet is folded along the bottom portion and the side wall portions, the second surface 122 is folded so that the folded parts face each other, and the first surface 121 is deformed so as to extend. At this time, since the fiber density on the first surface side is low and the gaps between the fibers before deformation are large, the first surface 121 is easily extended due to the decrease in the gaps. Therefore, the topsheet can be deformed along the fold, and is easily arranged along the bottom portion 111 and the side wall portions 112. In addition, since the fiber density on the second surface 122 side is high, the portion on the second surface 122 side tends to have a folding crease, and the state along the fold is easily maintained. As a result, the displacement of the absorbent sheet in the sheet accommodating portion 110 of the pet toilet 100 can be suppressed.

In the present specification, "fiber density" refers to the number of cut cross-sections of a fiber per unit area when a cut surface of a topsheet is observed under magnification. The measurement of the fiber density can be performed in the same manner as in the method described in JP 2012-144835 A (see paragraph 0041). Specifically, the fiber density can be measured according to the following [Measurement method for fiber density].

[Measurement Method for Fiber Density]

The number of cut cross-sections of fibers per a certain area (about 2 mm$^2$) when the cut surface of the topsheet is enlarged and observed with the midpoint in the thickness direction of the topsheet being the center of observation with use of a scanning electron microscope (for example, "Real Surface View Microscope VE-7800" manufactured by KEYENCE CORPORATION) (that is, observed at a magnification that allows observation of about 20 to 70 fiber cross sections and usually at a magnification of 20 to 100 times). The counted number of cut cross sections is converted into the number of cut cross sections of fiber per 1 mm$^2$, and this is defined as fiber density (numbers/mm²). The measurement of the fiber density is performed at a location, and the average value is used as the fiber density of a sample.

Further, in this specification, "surface roughness" refers to the roughness of the surface of a sheet. The mean deviation of surface roughness can be measured based on a characteristic value obtained with KES, manufactured by KATO TEC Co., Ltd., (Reference: Standardization and Analysis of Texture Evaluation (2nd edition), author: Sueo Kawabata, published on Jul. 10, 1980), which is generally known as a characteristic value representing the feel of the surface of the sheet.

Specifically, the surface roughness was measured by using KES-FB4 manufactured by KATO TECH Co., Ltd. and placing a specimen in a range of 1.0 to 1.0 cm in each sample on a test bed of a smooth metal plane. The surface roughness was measured by placing a load of 10 gf on the surface (or back surface) thereof and pressing a contact terminal having a width of 0.5 cm wound with a plano wire having a diameter of 0.5 mm on the sample. In the measurement of surface roughness, the specimen is moved 2 cm horizontally at a constant speed of 0.1 cm/sec, and a uniaxial tension of 20 gf/cm is given to the specimen. The surface roughness was obtained from the measurement results.

The folding line FL may be formed in the side regions SR. The side regions SR located on both sides of the central region CR in the second direction D2 are arranged over the entire region of the absorbent sheet 10 in the first direction D1. The absorbent sheet of one or more embodiments is configured such that the length of the first direction D1 is longer than the length of the second direction D2, and the side regions SR located on both sides of the central region CR in the second direction D2 are longer by at least 2 mm than the side regions SR located on both sides of the central region CR in the first direction D1. Therefore, when the side regions SR are arranged along the bottom portion 111 and the side wall portions 112 of the sheet accommodating portion 110, it may be difficult to maintain the standing state over the entire side regions SR. However, since the folding lines are formed in the side regions SR, the rigidity of the side regions SR increases due to the folding creases of the folding lines, and the standing state can be easily maintained. Therefore, the side regions SR can maintain the state arranged along the bottom portion 111 and the side wall portions 112, and the displacement of the absorbent sheet 10 in the pet toilet can be suppressed.

The topsheet 12 may have more fibers oriented along the first direction D1 than fibers oriented along the second direction D2. The side regions SR located on both sides of the central region CR in the second direction are arranged over the entire region of the absorbent sheet 10 in the first direction D1, and are longer than at least 2 mm than the side regions SR located on both sides of the central region CR in the first direction D1. Therefore, when the side regions SR are arranged along the bottom portion 111 and the side wall portions 112 of the sheet accommodating portion 110, it may be difficult to maintain the standing state over the entire side regions SR. However, a relatively large number of fibers are oriented along the second direction D2, and the side regions SR located on both sides of the central region CR in the first direction D1 can easily maintain the standing state in the second direction D2. Therefore, the side regions SR can maintain the state arranged along the bottom portion 111 and the side wall portions 112, and the displacement of the absorbent sheet 10 in the pet toilet can be suppressed.

Note that the fibers are oriented in the first direction (or the second direction) means that the fibers are oriented within a range of +45 degrees to −45 degrees with respect to the first direction (or the second direction). Further, the fiber orientation was measured using a digital microscope VHX-100 manufactured by KEYENCE CORPORATION by the following measurement method. (1) A sample is set on an observation table so that a surface of a convex wall portion can be observed, (2) a lens is focused on a fiber of the sample on the near side, excluding fibers that protrude irregularly to the near side, and (3) a 3D image of the sample is created on a PC screen. Next, (4) the 3D image is converted into a 2D image, and (5) a plurality of parallel lines that equally divides the thickness direction of the convex wall portion in a timely manner is drawn on the screen in the measurement range. (6) In each cell subdivided by drawing the parallel lines, the number of fibers facing in each direction is measured, and (7) for the total number of fibers in the set range, a ratio of the number of fibers having the fiber orientation in the thickness direction and a ratio of the number fibers having the fiber orientation in a direction perpendicular to the thickness direction are calculated. In this manner, the fiber orientation can be measured and calculated.

A plurality of joining portions 16 may be provided so as to extend in the second direction D2 and at intervals in the first direction D1. Since the joining portions 16 extending in the second direction are provided in the side regions SR, the rigidity along the second direction D2 is increased by the joining portions 16, and the standing state of the side regions SR is easily maintained. Further, since the plurality of joining portions is arranged at intervals in the first direction D1, the rigidity is increased over the entire area in the first direction D1, and the standing state can be easily maintained. Therefore, the side regions SR can maintain the state arranged along the bottom portion 111 and the side wall portions 112, and the displacement of the absorbent sheet 10 in the pet toilet can be suppressed. The joining portions 16 of one or more embodiments are provided in four rows at intervals in the first direction D1. Note that, although the joining portions 16 are provided in four rows, the number of rows is not limited, and may be provided on the entire surface of the absorbent sheet instead of the rows having intervals.

As shown in FIG. 3, a non-joining region NAR having no joining portion 16 may be provided at an outer edge portion of the side region SR in plan view. In the non-joining region NAR, the topsheet and the backsheet are easily deformed more flexibly in the side region SR than in the region where the topsheet 12 and the backsheet 14 are joined. When the absorbent sheet 10 is stored in the sheet accommodating portion or when the sheet accommodating portion is taken in and out, the non-joining region of the absorbent sheet 10 is locally deformed. Thus, the deformation of the entire absorbent sheet 10 is suppressed, and the displacement of the absorbent sheet 10 in the sheet accommodating portion can be suppressed.

The cover sheet 33 may cover the side surfaces of the absorbent core 30, and may be folded back to the top side of the absorbent core 30. The rigidity difference between the central region CR and the side regions SR is further increased by the presence or absence of the cover sheet 33 and the folding of the cover sheet 33. The side regions SR more easily raise with respect to the central region CR, and the side regions SR more easily follow the side wall portions 112 of the sheet accommodating portion 110.

The topsheet 12 may include a sheet containing an antimicrobial component. When the absorbent sheet 10 is arranged along the bottom portion 111 and the side wall portions 112, the absorbent sheet 10 bends at the fold as a base point. Excretions easily accumulate in the fold portion of the absorbent sheet 10, and bacteria are easily proliferated. Generally, the absorbent sheet 10 is not replaced by one excretion, but is used repeatedly, and may be used for about one week. In such a form of being repeatedly used, there is a fear that the growth of the bacteria becomes remarkable. Since the topsheet 12 includes a sheet containing an antibacterial component, an antibacterial function can be exhibited during the passage of the bodily fluid, and the growth of bacteria in the bodily fluid held by the absorbent sheet 10 can be suppressed. In the pet toilet, the excretion receiving portion 101 is provided above the sheet accommodating portion 110. A pet is excreted on the excretion receiving portion 101, and is difficult to directly touch the absorbent sheet 10 in the sheet accommodating portion 110. Therefore, it is possible to suppress the antibacterial component from directly touching the pet. The sheet containing the antibacterial component only needs to be provided with the antibacterial component on the topsheet, and various configurations can be adopted. For example, an antibacterial component may be provided to the fibers constituting the topsheet, or an antibacterial agent may be provided by spraying or the like after the topsheet is formed.

The absorbent core 30 may include an upper pulp layer 31 containing pulp, and a lower pulp layer 32 arranged on a side closer to the backsheet 14 than the upper pulp layer 31 and containing pulp. The upper pulp layer 31 allows the bodily fluid on the topsheet 12 to be quickly drawn in. Further, the drawn bodily fluid can be held by the lower pulp layer 32. The bodily fluid can be quickly guided from the topsheet 12 side which is closer to the pet to the backsheet 14 side which is farther from the pet.

As shown in FIG. 4, the upper pulp layer 31 includes only pulp and does not need to contain a superabsorbent polymer. The upper pulp layer 31 allows the bodily fluid drawn in from the topsheet 12 side to be quickly guided toward the lower pulp layer 32. In addition, the lower pulp layer 32 may contain pulp and superabsorbent polymers 35. The bodily fluid is easily drawn in by the superabsorbent polymers, and the bodily fluid can be more quickly guided toward the backsheet 14 side.

The absorber 20 may have the superabsorbent polymers 35 disposed between the upper pulp layer 31 and the lower pulp layer 32. The bodily fluid is easily drawn in by the superabsorbent polymers 35, and the bodily fluid can be more quickly guided toward the backsheet 14 side. Further, the absorber 20 may have an antibacterial agent 36 disposed between the upper pulp layer 31 and the lower pulp layer 32. The antibacterial function can be exhibited during the passage of the bodily fluid, and the growth of bacteria in the bodily fluid held by the absorbent sheet 10 can be suppressed. Further, the antibacterial agent may be disposed between the cover sheet 33 and the topsheet 12. The antibacterial function can be exhibited in the process of guiding the bodily fluid to the absorbent core 30, and the growth of bacteria in the bodily fluid held by the absorbent sheet 10 can be suppressed. Further, the absorber 20 may have deodorants 37. A deodorizing function can be exhibited during the passage of the bodily fluid. The deodorants 37 may be disposed between the cover sheet 33 and the topsheet 12, or between the upper pulp layer 31 and the lower pulp layer 32.

The antimicrobial may be in a powder form. In one or more embodiments, the antimicrobial may be formed from a powdery inorganic substance. Further, the powdery antimicrobial may be attached to a surface of the super absorbent polymer provided between the upper pulp layer 31 and the lower pulp layer 32. The antimicrobial may be an organic antimicrobial such as quaternary ammonium salt, p-oxybenzoic acid ester, etc. Alternatively, the antimicrobial may be an inorganic antimicrobial containing an inorganic substance such as Ag, Mn, Fe, Co, Ni, Cu, Zn, etc. Instead, the antimicrobial may be an antibacterial substance containing a natural material such as a tea leave, a coffee extraction residue, etc. The bacteriostat may be a bacteriostatic substance such as organic acid, organic acid salt, etc. In addition, the above-described antibacterial and bacteriostatic substances may be mixed with each other. The antibacterial agent of one or more embodiments is composed of osmorin.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

According to one or more embodiments of the present invention, it is possible to provide an absorbent sheet for pets that can suppress displacement in a pet toilet.

10: absorbent sheet
10P: front surface
12: topsheet
121: first surface
122: second surface
14: backsheet
16: joining portions
20: absorber
30: absorbent core
31: upper pulp layer
32: lower pulp layer
90: absorbent sheet
100: pet toilet
101: excretion receiving portion
110: sheet accommodating portion
111: bottom portion
112: side wall portions
D1: first direction
D2: second direction
FL: folding line
NAR: non-joining region

What is claimed is:

1. An absorbent sheet for a pet toilet, including a sheet accommodating portion that accommodates the absorbent sheet in a space surrounded by a bottom portion and side walls standing from the bottom portion, and an excretion receiving portion that receives excretions above the sheet accommodating portion and guides the excretions to the sheet accommodating portion, the absorbent sheet comprising:

a topsheet on a top side of the absorbent sheet and that comprises fibers;
a backsheet on a back side of the absorbent sheet;
an absorber between the topsheet and the backsheet;
a central region in which the absorber is disposed in plan view; and
side regions that extend outside the central region and in which at least the topsheet is disposed, wherein
the topsheet has a first surface and a second surface opposite to the first surface,
a fiber density of a region on a side of the first surface is lower than a fiber density of a region on a side of the second surface, a surface roughness of the first surface is higher than a surface roughness of the second surface,
the absorbent sheet has a thickness direction, a first direction perpendicular to the thickness direction, and a second direction perpendicular to the thickness direction and the first direction,
a length of the absorbent sheet in the first direction is longer than a length of the absorbent sheet in the second direction,
the side regions cover an entire region of the absorbent sheet in the first direction on both sides, in the second direction, of the central region, and
the topsheet has more fibers oriented along the second direction than fibers oriented along the first direction.

2. The absorbent sheet according to claim 1, wherein
before use, the absorbent sheet is folded along a folding line extending in the second direction, and
the folding line is in the side regions.

3. The absorbent sheet according to claim 1, wherein
the absorbent sheet further comprises joining portions that:
join the topsheet and the backsheet, and
extend in the second direction in the side regions, and are disposed at intervals in the first direction.

4. The absorbent sheet according to claim 1, wherein
the absorbent sheet further comprises joining portions that join the topsheet and the backsheet, and
a non-joining region without joining portions is disposed, in plan view, at an outer edge of the side regions.

5. The absorbent sheet according to claim 1, wherein
the absorber comprises an absorbent core and a cover sheet between the topsheet and the absorbent core, and
the cover sheet covers side surfaces of the absorbent core, and is folded toward a top side of the absorbent core.

6. The absorbent sheet according to claim 1, wherein the topsheet includes a sheet containing an antimicrobial component.

7. The absorbent sheet according to claim 6, wherein
the absorber includes an absorbent core, and
the absorbent core includes:
an upper pulp layer containing pulp, and
a lower pulp layer containing the pulp and that is on a side closer to the backsheet than the upper pulp layer.

8. The absorbent sheet according to claim 7, wherein the absorber has a superabsorbent polymer disposed between the upper pulp layer and the lower pulp layer.

9. The absorbent sheet according to claim 2, wherein
the absorbent sheet further comprises joining portions that:
join the topsheet and the backsheet, and
extend in the second direction in the side regions, and are disposed at intervals in the first direction.

10. The absorbent sheet according to claim 2, wherein
the absorbent sheet further comprises joining portions that join the topsheet and the backsheet, and
a non-joining region without joining portions is disposed, in plan view, at an outer edge of the side regions.

11. The absorbent sheet according to claim 3, wherein
the absorbent sheet further comprises joining portions that join the topsheet and the backsheet, and
a non-joining region without joining portions is disposed, in plan view, at an outer edge of the side regions.

12. The absorbent sheet according to claim 2, wherein
the absorber comprises an absorbent core and a cover sheet between the topsheet and the absorbent core, and
the cover sheet covers side surfaces of the absorbent core, and is folded toward a top side of the absorbent core.

13. The absorbent sheet according to claim 3, wherein
the absorber comprises an absorbent core and a cover sheet between the topsheet and the absorbent core, and
the cover sheet covers side surfaces of the absorbent core, and is folded toward a top side of the absorbent core.

14. The absorbent sheet according to claim 4, wherein
the absorber comprises an absorbent core and a cover sheet between the topsheet and the absorbent core, and
the cover sheet covers side surfaces of the absorbent core, and is folded toward a top side of the absorbent core.

15. The absorbent sheet according to claim 2, wherein the topsheet includes a sheet containing an antimicrobial component.

16. The absorbent sheet according to claim 3, wherein the topsheet includes a sheet containing an antimicrobial component.

17. The absorbent sheet according to claim 4, wherein the topsheet includes a sheet containing an antimicrobial component.

18. The absorbent sheet according to claim 5, wherein the topsheet includes a sheet containing an antimicrobial component.

* * * * *